(12) United States Patent
Strong (10) Patent No.: US 8,124,053 B2
(45) Date of Patent: Feb. 28, 2012

(54) COMPOSITIONS COMPRISING CHITIN MICROPARTICLES AND THEIR MEDICAL USES

(75) Inventor: Peter Strong, Bicester (GB)

(73) Assignee: CMP Therapeutics Limited, Bicester (GB)

( * ) Notice: Subject to any disclaimer, the term of this patent is extended or adjusted under 35 U.S.C. 154(b) by 18 days.

(21) Appl. No.: 12/339,849

(22) Filed: Dec. 19, 2008

(65) Prior Publication Data

US 2009/0209905 A1 Aug. 20, 2009

Related U.S. Application Data

(63) Continuation-in-part of application No. PCT/GB2007/002188, filed on Jun. 13, 2007.

(60) Provisional application No. 60/815,074, filed on Jun. 20, 2006.

(51) Int. Cl.
- A61K 48/00 (2006.01)
- A61K 47/30 (2006.01)
- A01N 63/00 (2006.01)

(52) U.S. Cl. ...................... 424/1.69; 424/93.1

(58) Field of Classification Search ............ None
See application file for complete search history.

(56) References Cited

U.S. PATENT DOCUMENTS

| | | | |
|---|---|---|---|
| 5,591,441 A | 1/1997 | Gristina et al. | |
| 2008/0014281 A1 * | 1/2008 | Shibata et al. | 424/499 |

FOREIGN PATENT DOCUMENTS

| | | |
|---|---|---|
| JP | 10-279606 | 10/1998 |
| WO | WO 90/09780 | 9/1990 |
| WO | WO 97/20576 | 6/1997 |
| WO | WO 98/30207 | 7/1998 |
| WO | WO 03/015744 | 2/2003 |

OTHER PUBLICATIONS

Shibata et al. Infection and Immunity Oct. 2001, vol. 69 (10), pp. 6123-6130.*
Yasuko Asahi-Ozaki, et al., Intranasal Administration of Adjuvant-Combined Recombinant Influenza Virus HA Vaccine Protects Mice From the Lethal H5N1 Infection, Microbes and Infection (2006) vol. 8, p. 2706-2714.
Hideki Hasegawa, et al., Protection Against Influenza Virus Infection by Intranasal Administration of Hemagglutinin Vaccine With Chitin Microparticles as an Adjuvant, Journal of Medical Virology (2005) vol. 75 p. 130-136.
Keiko Nishimura, et al., Effect of Multiporous Microspheres Derived From Chitin and Partially Deacetylated Chitin on the Activation of Mouse Peritoneal Macrophages, Vaccine (1987) vol. 5, p. 136-140.
C. Ozdemir, et al., Treatment With Chitin Microparticles is Protective Against Lung Histopathology in a Murine Asthma Model, Clinical and Experimental Allergy (2006) vol. 36, p. 960-968.
Yoshimi Shibata, et al., Chitin Particle-Induced Cell-Mediated Immunity is Inhibited by Soluble Mannan, Journal of Immunology (1997) vol. 159, p. 2462-2467.
Yoshimi Shibata, et al., Th1 Adjuvant N-Acetyl-D-Glucosamine Polymer Up-Regulates Th1 Immunity but Down-Regulates Th2 Immunity Against a Mycobacterial Protein (MPB-59) in Interleukin-10 Knockout and Wild-Type Mice, Infection and Immunity (2001) vol. 69, No. 10, p. 6123-6130.
Yoshimi Shibata, et al., Oral Administration of Chitin Down-Regulates Serum IgE Levels and Lung Eosinophilia in Allergic Mouse[1], Journal of Immunology (2000) vol. 164, p. 1314-1321.
Yoshimi Shibata, et al., Alveolar Macrophage Priming by Intravenous Administration of Chitin Particles, Polymers of N-Acetyl-D-Glucosamine, in Mice, Infection and Immunity (1997) vol. 65, No. 5, p. 1734-1741.
Peter Strong, et al., Intranasal Application of Chitin Microparticles Down-Regulates Symptoms of Allergic Hypersensitivity to *Dermatophagoides pteronyssinus* and *Aspergillus fumigatus* in Murine Models of Allergy, Clin. Exp. Allergy (2002) vol. 32, p. 1794-1800.
Julian Davies, Bacterial on the Rampage (1996) vol. 383. p. 219-220.
Hisashi Fujioka, et al., The Malaria Parasite and its Life-Cycle, Malaria: Molecular and Clinical Aspects, Eds. Mats Wahlgren and Peter Perlmann, Overseas Publishers Association: Amsterdam, Netherlands, 1999, 19-55.
Chakrit Hirunpetcharat, et al., Malaria Parasite:-Specific Th1-Like Cells Simultaneously Reduce Parasitemia and Promote Disease, Parasite Immunology (1999) vol, 21, p. 319-329.
Teresa C. Horan, et al., Nosocomial Infection Survelliance, 1984: 1986 / 35(SS-I); p. 17-29 http//www.cdc.gov/mmwr/preview/mmwrhtml/00001772.htm.
Yogesh K. Katare, et al., Immunogenicity and Lower Dose Requirement of Polymer Entrapped Tetanus Toxoid Co-Administered With Alum; Vaccine (2006) vol. 24, p. 3599-3608.
Yoshimi Shibata, et al., Immuoregulatory Roles of IL-10 in Innate Immunity: IL-10 Inhibits Macrophage Production of IFN-γ-Inducing Factors but Enhances NK Cell Production of IFN-γ[1], Journal of Immunology (1998) vol. 161, p. 4283-4288.
Wasim A. Siddiqui, et al., Merozoite Surface Coat Precursor Protein Completely Protects *Aotus* Monkeys Against *Plasmodium falciparum* Malaria, PNAS (1987) vol. 84, p. 3014-3018.
Jim Vadolas, et al., Intranasal Immunization With Liposomes Induces Strong Mucosal Immune Responses in Mice, Eur. J. Immunol. (1995) vol. 25, p. 969-975.

\* cited by examiner

*Primary Examiner* — Bao Li
(74) *Attorney, Agent, or Firm* — Vedder Price P.C.; Thomas J. Kowalski; Deborah L. Lu (57) ABSTRACT

The present invention relates to compositions comprising chitin microparticles and their medical uses, and in particular to compositions for use as vaccines which comprise antigen from an infectious agent, a chitin microparticle preparation, and a further adjuvant.

37 Claims, 2 Drawing Sheets

COMPOSITIONS COMPRISING CHITIN MICROPARTICLES AND THEIR MEDICAL USES

INCORPORATION BY REFERENCE

This application is a continuation-in-part application of international patent application Serial No. PCT/GB2007/002188 filed Jun. 13, 2007, published as WO 2007/14808 on Dec. 27, 2007, which claims priority to U.S. provisional application Ser. No. 60/815,074 filed Jun. 20, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to compositions comprising chitin microparticles and their medical uses, and in particular to compositions for use as vaccines which comprise antigen from an infectious agent, a chitin microparticle preparation, and a further adjuvant.

BACKGROUND OF THE INVENTION

There is a continuing need in the art to develop new ways of treating and/or preventing infection by pathogens. Broadly speaking, vaccines in the art are based on inactivated or attenuated infectious agents or synthetic antigens that are administered to patients in a primary immunization followed by a secondary booster immunization normally given to a patient several weeks after the primary inoculation in order to provide the necessary protective immunity in the patient. While adjuvants are often included in vaccine compositions to enhance the immune response, comparatively few adjuvants have been approved for use in vaccines administered to humans. There is a particular need for safe adjuvants that can be delivered by the nasal route or by inhalation. Nasal vaccines have a particular usefulness because they can be self-administered and does not require a clinician. This is advantageous in mass vaccination programs or in the developing countries where there is a shortage of trained personnel.

Studies by Shibata et al. (1-4) have shown that oral delivery of 1-10 μm phagocytosable chitin particles results in an elevation of Th1 cytokines in mouse spleen cell cultures. The effect was specific to particulates as no elevation was produced by soluble chitin. It could also be reproduced using 1 μm polystyrene microspheres coated with N-Acetyl-D-Glucosamine, which is the main component of chitin. It was also demonstrated that oral administration of chitin down-regulates serum immunoglobulin E (IgE) and lung eosinophilia in a murine model of ragweed allergy (1).

Shibata et al. have also developed a mouse model of allergic airway inflammation and orally administered chitin preparations to the mice (1). Ragweed-specific IgE levels were significantly reduced after daily oral administration of chitin to ragweed-sensitized mice, before and during immunization. Bronchioalveolar lavage (BAL) cells were harvested 14 days after immunization and a reduction in the levels of eosinophil and lymphocyte levels was observed after chitin treatment. Lung inflammation was determined histologically 14 days after immunization, and peribronchial, perivascular, and total lung inflammation were inhibited in the chitin-treated group.

When chitin was administered prophylactically to mice who were subsequently administered ragweed, IL-4, IL-5, and IL-10 production was significantly reduced and low, although significant levels of IFN-γ were detected. Chitin also has a prophylactic effect when administered to C57BL6 mice, which are considered higher responders for cell-mediated immunity/Th1 responses, but lower responders for allergic responses, compared with BALB/c mice. When ragweed-sensitized mice were treated simultaneously with ragweed and chitin, the resulting levels of IL-4, IL-5, and IL-10 were significantly reduced compared to those stimulated by ragweed alone.

However, while Shibata et al. disclose the use of chitin microparticles for the treatment of allergy, the compositions are administered orally as a supplement to activate macrophages and prophylactically strengthen the immune system in the absence of recurrent bacterial infections that are decreasingly common in industrialized countries.

Japanese Patent Application No. 19997-0087986 A (Unitika Limited) discloses the use of deacetylated chitin particles (e.g., chitosan compositions) in the form of powders, granules, or fibres for delivery to the nasal mucosa. The chitosan particles have an effective particle diameter of 20 to 250 microns and are proposed for the treatment of allergic symptoms at an inflammatory site such as pollinosis.

U.S. Pat. No. 5,591,441 9 (Medical Sciences Research Institute) concerns the use of particulate compositions for providing protection against microorganism infection and biological warfare agents. The compositions are delivered intravenously with the aim of providing a short lived increased in in vivo peroxide levels to kill the microorganisms.

In our earlier patent application WO 03/015744, we describe the use of chitin microparticle preparations (CMP) for the treatment of allergy, conditions benefiting from an up-regulation of the cell mediated immune system, such as bacterial infection, fungal infection, and viral infection, and conditions that would benefit from an up-regulation of natural killer (NK) cell activity and/or the secretion of interferon-γ (IFN-γ), such as the treatment of cancer.

Danbiosyst has filed patent applications in which chitosan, a deacetylated form of chitin, is used as a drug delivery system, in particular for targeting the mucosa of patients. WO 98/30207 relates to the use of chitosan for transporting active agents across mucosa using compositions comprising chitosan, type A cationic gelatin, and a therapeutic agent. WO 97/20576 relates to the use of chitosan as an adjuvant for intranasal administration with an antigen with the aim of improving the antigenicity of the antigen when the composition is used to immunize a subject. WO 90/09780 discloses the use of microcapsules containing chitosan for drug delivery across mucosa. Chitosan is described in these applications as being produced from chitin by a hydrolysis reaction in which the greater proportion of the N-acetyl groups in chitin are removed, typically providing levels of deacetylation of about 90%.

There are many examples in the art where there are opportunities for improving the protection afforded to individuals through the development or improvement of vaccine compositions. The following are examples wherein there is a need for more effective protection.

*Pseudomonas aeruginosa*, an opportunistic pathogen, is a leading cause of life threatening infections in immunocompromised individuals and is a major risk to patients on ventilator support and/or suffering from many disease conditions in which there is a reduction in lung function and a reduced ability to clear infections. Each year, over two million patients die as a result. A report on the incidence of hospital-associated infections places *P. aeruginosa* among the three most frequently reported pathogens (5). *P. aeruginosa* is also a common cause of chronic and life threatening pulmonary infection in cystic fibrosis patients. Recent reports list *P. aeruginosa* among the most serious antibiotic-resistant bacteria and one for which effective vaccines are needed (6).

*Streptococcus pneumoniae* is a ubiquitous pathogen and responsible for a high proportion of cases of pneumonia (both lobar and bronchopneumonia). It is one of the leading causes of illness and death among young children, the elderly and those with an impaired immune system as the result of diseases such as AIDS, or immunosuppressive therapy such as for bone marrow transplantation. The invasive form of Streptococcal infection, in which the bacteria disseminate into the blood and other organs leads to very serious complications. Each year in the United States, pneumococcal disease is estimated to cause 3000 cases of meningitis, 50,000 cases of bacteraemia, 125,000 hospitalizations and 6,000,000 cases of Otitis media. There is also a growing concern about the emergence of antibiotic resistant strains of *S. pneumoniae*.

Recently, risk of influenza pandemics, for example arising from avian influenza, has raised awareness of the need for effective prevention and treatment of infection in the population.

Furthermore, in the Third World, the population is exposed to many infectious agents and infection might be prevented or ameliorated by the development of effective and economic vaccines. Examples of conditions that might be treatable include malaria. Malaria, a parasitic infection, is an important cause of mortality and morbidity in many parts of the world. It affects 300-500 million people and kills 1-2 million each year, mostly children under the age of 5 years. Malaria has a devastating effect on economic development in the Third World. The recent appearance of drug-resistant strains is causing great concern and the changes in global climate are presenting an elevated incidence in developed countries as well.

It would be a considerable advantage in these countries to have available vaccines that are capable of providing protection after a course of administration over a short period of time to help to avoid the need for a secondary booster inoculation several weeks after the primary inoculation.

SUMMARY OF THE INVENTION

Broadly, the present invention relates to compositions comprising chitin microparticles and their medical uses, and in particular to compositions for use as vaccines comprising an antigen from an infectious agent and a chitin microparticle (CMP) preparation comprising CMP. The CMP preparation, in some embodiments, may act as an adjuvant. In preferred aspects of the present invention, the compositions comprise a further adjuvant, i.e., an adjuvant which is different than the CMP preparation. The results presented herein show that CMP are capable of acting as adjuvants in vaccine or pharmaceutical compositions, as compared to the results disclosed in WO 03/015744, which shows that CMP compositions are capable of providing broad-based up-regulation of the immune system when used alone. The present invention also shows that CMP preparations are capable of synergistically enhancing the protection raised against an antigen from an infectious agent when the CMP preparation is combined with a further adjuvant. In a further aspect, the present invention shows that the administration of the disclosed compositions multiple times per week (e.g., at least two, or more preferably three or more, times per week) enhances the protective response raised against the infectious agent when compared to a more usual pattern of administration in which an initial immunization is followed by a secondary booster after a gap of several weeks.

Accordingly, in a first aspect, the present invention provides a composition comprising an antigen from an infectious agent, a CMP preparation, and a further adjuvant. These compositions can be employed in the prophylaxis and treatment of infections and associated symptoms. The antigen may be natural, synthetic, or derived by recombinant DNA technology. In some embodiments, the CMP preparation may be a first adjuvant, and the further adjuvant may be a second adjuvant.

The composition may be a vaccine composition. It may therefore contain an antigen, consisting of whole organisms, either killed or weakened, or parts of such organisms, which are used to confer immunity against the condition that the organism causes. By way of example, the infectious agent may cause a bacterial infection, a fungal infection, a viral infection, or a parasitic infection.

In a further aspect, the present invention provides a composition as defined herein for use in therapy and in particular for the prophylaxis or treatment of a condition caused by an infectious agent.

In a further aspect, the invention provides the use of a composition comprising an antigen from an infectious agent, a CMP preparation, and a further adjuvant for the preparation of a medicament for the prophylaxis or treatment of a condition mediated by the infectious agent. The infectious agent may cause a bacterial infection, a fungal infection, a viral infection, or a parasitic infection. In some embodiments, the CMP preparation may be a first adjuvant, and the further adjuvant may be a second adjuvant.

In a further aspect, the present invention provides a method for vaccinating a patient against a condition mediated by an infectious agent, the method comprising administering to a patient in need thereof a therapeutically or prophylactically effective amount of the composition as defined herein Examples of other adjuvants that may be employed in the compositions with the CMP preparations include, but are not limited to, adjuvants based on cholera toxins such as cholera holotoxin (CT) or cholera toxin B subunit (CTB), synthetic CpG DNA, and adjuvants based on bacterial cell wall products.

Advantageously, the examples provided herein show that an administration pattern in which the compositions of the invention are administered at least two times per week, and more preferably at least three times per week, enhance the protective response raised against the infectious agent when compared to a more usual pattern of administration in which an initial immunization is followed by a secondary booster after a gap of several weeks.

In the present invention, a range of delivery routes may be used for delivering the compositions to individuals in need of vaccination. Preferably, these include, but are not limited to, delivery by the sub-lingual or oral routes, by injection (e.g., subcutaneous injection or intramuscular injection), intranasally (e.g., to the sinuses and upper respiratory tract using an intranasal spray), or by inhalation (e.g., targeting alveolar macrophages in the lungs).

The compositions may be administered to a patient via a mucosal or a non-mucosal delivery route. Mucosal delivery routes include, but are not limited to, sublingual delivery to, as an example, buccal mucosa; oral delivery to, for instance, gut mucosa; delivery in eye drops to, for example, eye mucosa; intranasal delivery to, for instance, nose mucosa and mucosa of the upper respiratory tract; and delivery by inhalation to, as an example, mucosa of the upper and lower respiratory tract such as lung mucosa. Non-mucosal delivery routes include, but are not limited to, delivery by injection, for example, by subcutaneous injection or intramuscular injection.

In some aspects of the present invention mucosal delivery routes are preferred as they are advantageous due to their safety; ease of administration, as they do not generally require a clinician to administer the vaccination (in contrast to injection); ease of distribution; reduced production cost; and improved immunological response, as mucosal delivery may activate both the cellular and humoral immune responses.

In another aspect, the present invention provides a kit comprising:
a) a chitin microparticle composition;
b) an antigen from an infectious agent; and
c) a further adjuvant;
for simultaneous or sequential administration to a patient for providing immunity against the condition caused by the infectious organism. The kit may further comprise a delivery device.

In a further aspect, the present invention provides a delivery device comprising a reservoir of CMP preparation as defined herein, and a delivery orifice adapted to locate in a patient's mouth or nose, wherein the patient can place the delivery orifice in the mouth or nose to administer the CMP preparation. In some embodiments the device may comprise a valve between the reservoir and the delivery orifice, such that the valve can be operated to control delivery of the CMP preparation. The microparticles may be drawn into the nose to the sinuses and upper respiratory tract, or through the mouth to alveolar macrophages by inhalation and/or by a propellant. In some embodiments, the device is a nasal spray bottle containing a CMP preparation and optionally a carrier, the spray bottle having a neck adapted for nasal delivery.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings in which.

DETAILED DESCRIPTION

Chitin Microparticles

Chitin is a polymer of N-acetyl-D-glucosamine. It is an abundant polysaccharide in nature, comprising the horny substance in the exoskeletons of crab, shrimp, lobster, cuttlefish, and insects, as well as fungi. A readily available and preferred source of chitin is from shrimp shells. Any of these or other sources of chitin are suitable for the preparation of CMP preparations for use according to the present invention. Alternatively, the CMP may be synthesized by chemical or enzymatic techniques as an alternative to natural source extraction. This approach would have the advantage of providing a more homogeneous product.

Preferably, chitin is produced by physically reducing it, e.g., by sonication or milling, to particles having a diameter of less than 50 µm, more preferably less than 40 µm, still more preferably less than 20 µm, more preferably less than 10 µm and most preferably less than 5 µm. As we have found that the effects caused by CMP may be size-dependent, in some embodiments, CMP have average diameters that are less than 10 µm. An upper limit of chitin particles size may be functionally defined by macrophages not recognizing the particles. The lower size limit may not be as critical, but preferably the particles are at least 1 µm in diameter. The lower size limit is functionally defined by the chitin particles becoming soluble and, hence, not being recognized by macrophages as well. Particles size and size distribution can readily be determined by the skilled person, for example, using flow cytometry or a microscope. Alternatively or additionally, CMP can be made by coating carrier particles, e.g., formed from a biocompatible material such as polystyrene or latex, with N-Acetyl-D-Glucosamine, chitin or a fragment thereof, to form particles having the sizes as defined above. These preparations may be included within the term CMP preparation as used herein.

It should be recognized that in a preparation, the CMP may have a distribution of sizes, typically a normal distribution, and that not all particles within a population will necessarily meet these size limits. However, within a population of CMP forming a CMP preparation, preferably at least 60%, more preferably at least 75%, more preferably at least 90%, and more preferably 95% and most preferably at least 99%, of the chitin particles have a size distribution within the limits set out above.

It will also be recognized by those skilled in the art that chitosan is a different material to the chitin used to make the CMP preparations used in the present invention in that the polysaccharide units in chitosan are substantially deacetylated. As chitin is derived from a natural material, there is a variation in its composition and there may be low levels of deacetylated units that naturally occur in the chitin polymer. However, it is preferred in the CMP preparations of the present invention that the deactylated units in the chitin composition comprise less than 20% of the total units, more preferably less than 15% of the total units, more preferably less than 10% of the total units, and most preferably less than 5% of the total units.

Pharmaceutical Compositions

In addition to the CMP preparation discussed above, a composition (or "pharmaceutical composition") according to the present invention may further comprise an antigen from an infectious agent. The infectious agent may mediate a bacterial infection, a fungal infection, a viral infection, or a parasitic infection. As discussed herein, the combination of a CMP preparation with a further, different adjuvant, and an antigen may provide compositions that provide synergistic responses useful for the treatment or prevention of infections by the infectious agent.

In preferred embodiments, the compositions of the present invention may be employed for the treatment or prevention of malaria, influenza, or HIV.

Examples of antigens and vaccine that can be employed in accordance with the present invention include, but are not limited to, influenza hemagglutinin (HA) vaccines prepared from inactivated virus such as H5N1, H1N1, H3N2; HIV vaccines containing HIV-DNA or HIV antigens; anthrax vaccines such as those containing recombinant Protective Antigen (PA); haemophilus influenza antigens; and human papilloma virus antigens such as E7 protein.

In common with many infectious agents, antigens suitable for inclusion in compositions for vaccinating against malaria are known in the art.

In malaria, the merozoite is the blood borne form of the parasite life cycle prior to infection of the red blood cells. Merozoite surface protein 1 (MSP1) is recognized as a promising malaria vaccine candidate and has been tested as a vaccine candidate in several studies (Siddiqui et al. Merozoite surface coat precursor protein completely protects *Aotus* monkeys against *Plasmodium falciparum* malaria. *Proc. Natl. Acad. Sci. USA* 1987 84: 3014). Efficacy has also been demonstrated in mice immunized intranasally (Hirunpetcharat et al., Parasite Immunology. 1998, vol. 20, issue 9). MSP1 is involved in the initial recognition and attachment of the merozoite to red blood cells (Fujioka, et al., The malaria parasite and its life cycle. In: Wahlgren M, Perlmann P, (eds) *Malaria: Molecular and Clinical Aspects*. Amsterdam: Harwood Academic Publishers, 1999, 19).

Antibodies against MSP neutralize the parasite by agglutinating or opsonizing merozoites, thereby preventing them from invading red blood cells at the initial infection and during amplification stages of the disease. During the parasite life cycle, the MSP1 protein is cleaved into smaller fragments including the C-terminal fragment called $MSP1_{19}$. This 19 kDa peptide fragment is highly conserved within *Plasmodium* spp, including *P. yoelii*, a strain that infects mice, making it an ideal target for a malaria vaccine. $MSP1_{19}$ can be produced as a recombinant protein using a yeast expression system.

However, recombinant subunit vaccines are poorly immunogenic and require the addition of appropriate adjuvants to produce an optimal IgG titre. The inability to identify suitable adjuvants is a significant impediment to the development of a malaria vaccine and this is a particular problem for vaccines delivered to mucosal surfaces such as a nasal vaccine. The advantage of a mucosal vaccine includes better toleration and the possibility of eliciting a more robust protective response involving both humoral and cellular immune responses. For mass vaccination, a nasal vaccine has the advantages of requiring minimal clinical personnel for its administration.

As detailed herein, it is preferred that the CMP preparation is employed in combination with a further different adjuvant. Examples of other adjuvants that might be employed in the compositions with the CMP preparations include, but are not limited to, adjuvants based on cholera toxins such as cholera holotoxin (CT) or cholera toxin B subunit (CTB), synthetic CpG DNA, and adjuvants based on bacterial cell wall products. The use of adjuvants is reviewed in F. Vogel, M. Powell and C. Irving, "A Compendium of Vaccine Adjuvants and Excipients (2nd Edition)", available on the NIH website.

Cholera toxin subunit B (CTB) is a potent mucosal adjuvant, although it can produce unwanted side effects. These side effects can be reduced by adding small amounts (0.1-2%) of the cholera holotoxin. CTB stimulates the local mucosal cellular immune response as well as the systemic IgG response, and is commonly used in experimental nasal vaccines (Vadolas et al. *Eur J Immunol* 1995, 25: 969).

Examples of bacteria-derived adjuvants include, but are not limited to, peptidoglycan or lipopolysaccharide derivatives such as muramyl-L-alanyl-D-isoglutamine (MDP), monophosphoryl lipid A (MPL), trehalose dimycolate (TDM), cholera toxin B subunit (CTB), CpG DNA, and immunostimulatory cytokines including IL-12 and IFN and GM-CSF.

It has been reported in the art that adjuvants may have a synergistic effect when administered together in the same vaccine formulation. However, prior to the present invention, it was not known that CMP could possess this synergistic activity when combined with other adjuvants in vaccine formulations.

In addition to CMP, antigen and adjuvants, the compositions may comprise one or more of a pharmaceutically acceptable excipient, carrier, propellant, buffer, stabilizer, isotonicizing agent, preservative or anti-oxidant, or other materials well known to those skilled in the art. Such materials should be non-toxic and should not interfere with the efficacy of the active ingredient.

Preservatives are generally included in pharmaceutical compositions to retard microbial growth, extending the shelf life of the compositions and allowing multiple use packaging. Examples of preservatives include, but are not limited to, phenol, meta-cresol, benzyl alcohol, para-hydroxybenzoic acid and its esters, methyl paraben, propyl paraben, benzalconium chloride, and benzethonium chloride. Preservatives are typically employed in the range of about 0.1% to 1.0% (w/v).

Preferably, the pharmaceutical compositions may be given to an individual in a "prophylactically effective amount" or a "therapeutically effective amount" (as the case may be, although prophylaxis may be considered therapy), this amount being sufficient to show benefit to the individual, e.g., providing alleviation of allergy or another condition or prophylaxis for an acceptable period. Typically, this may be to cause a therapeutically useful activity providing benefit to the individual. The actual amount of the compounds administered, and rate and time-course of administration, may depend on the nature and severity of the condition being treated. Prescription of treatment, e.g., decisions on dosage, etc., may be within the responsibility of general practitioners and other medical doctors, and typically may take into account the disorder to be treated, the condition of the individual patient, the site of delivery, the method of administration and other factors known to practitioners. Examples of the techniques and protocols mentioned above may be found in Remington's Pharmaceutical Sciences, 16th edition, Osol, A. (ed), 1980, and Remington's Pharmaceutical Sciences, 19th edition, Mack Publishing Company, 1995. The compositions may be preferably administered in dosages of between about 0.01 and 100 mg of active compound per kg of body weight, and more preferably between about 0.5 and 10 mg/kg of body weight. By way of example, this may be achieved using a nasal delivery bottle to deliver 4-8 doses of approximately 0.25 ml of a 5 mg/ml solution of CMP particles.

Infectious Agent

The compositions described herein are applicable for use in the treatment or prevention of a range of conditions caused by the infection of an individual by an infectious agent.

Broadly speaking, infectious agents include a range of microscopic organisms such as bacteria, viruses, parasites, and fungi. A range of antigens from infectious agent or inactivated forms of the agents that are known, and further examples that are developed by those skilled in the art, may be used in compositions for protecting or treating individuals in combination with a CMP adjuvant as disclosed herein, and optionally one or more further adjuvants. In preferred embodiments, the present invention may be used for the treatment or prevention of malaria, HIV or influenza.

By way of example, diseases or conditions caused by viral infectious agents include, but are not limited to, AIDS, AIDS related complex, chickenpox (Varicella), common cold, cytomegalovirus infection, Colorado tick fever, Dengue fever, Ebola haemorrhagic fever, epidemic parotitis, flu, hand, foot and mouth disease, hepatitis, herpes simplex, herpes zoster, human papillomaviruses, influenza, lassa fever, measles, Marburg haemorrhagic fever, infectious mononucleosis, mumps, poliomyelitis, progressive multifocal leukencephalopathy, rabies, rubella, severe acute respiratory syndrome (SARS), smallpox (Variola), viral encephalitis, viral gastroenteritis, viral meningitis, viral pneumonia, West Nile disease, and yellow fever.

By way of example, diseases or conditions caused by bacterial infectious agents include, but are not limited to, anthrax, bacterial meningitis, brucellosis, bubonic plague, Campylobacteriosis, cholera, diphtheria, epidemic typhus, gonorrhea, impetigo, Hansen's disease, legionella, leprosy, leptospirosis, listeriosis, Lyme's disease, melioidosis, MRSA infection, nocardiosis, pertussis, pneumococcal pneumonia, psittacosis, Q fever, Rocky Mountain spotted fever (RMSF), salmonellosis, scarlet fever, shigellosis, syphilis, tetanus, trachoma, tuberculosis, tularemia, typhoid fever, typhus, and whooping cough.

By way of example, diseases or conditions caused by parasitic infectious diseases include, but are not limited to, African trypanosomiasis, amebiasis, amoebic infection, ascariasis, babesiosis, Chagas disease, clonorchiasis, cryptosporidiosis, cysticercosis, diphyllobothriasis, dracunculiasis, echinococcosis, enterobiasis, fascioliasis, fasciolopsiasis, filariasis, giardiasis, gnathostomiasis, hymenolepiasis, isosporiasis, kala-azar, leishmaniasis, malaria, metagonimiasis, myiasis, onchocerciasis, pediculosis, scabies, schistosomiasis, taeniasis, toxocariasis, toxoplasmosis, trichinellosis, trichinosis, trichuriasis, and trypanosomiasis.

By way of example, diseases or conditions caused by fungal infectious diseases include, but are not limited to, Aspergillosis, Blastomycosis, Candidiasis, Coccidioidomycosis, Cryptococcosis, Histoplasmosis, and Tinea pedis.

The present invention may be applicable to the treatment of microbial infections, including bacterial infections, fungal infections and viral infections, particularly among vulnerable patient groups such as the elderly, premature babies, infants, transplantation patients, immunosuppressed patients such as chemotherapy patients, hospital patients at risk of opportunistic infection, patients on ventilators, cystic fibrosis patients, and patients with AIDS. The invention may be particularly applicable to the treatment of ear, nose, throat and lung infections.

Specific examples of bacterial infection include, but are not limited to, the treatment of infection by microorganisms such as *Pseudomonas aeruginosa; Streptococcus* species such as *Streptococcus pneumoniae, Streptococcus pyrogenes*, and *Streptococcus agalactiae; Haemophilus influenza; Klebsiella pneumoniae; Yersinia enteocolitica; Salmonella; Listeria; Mycobacterial* infections including *Mycobacterium tuberculosis*, and *Mycobacterium leprae*; and parasitic infections including *Leishmania* species and *Schistosoma* species.

One condition caused by microbial infection, typically by *Streptococcus pneumoniae*, is recurrent ear infections such as Otitis media. These conditions occur in children and adults and are currently treated using antibiotics. It may be advantageous to use the pharmaceutical compositions of the invention to treat these conditions and reduce the need for antibiotics.

The compositions of the invention may be used in the treatment of tuberculosis either to treat an existing infection or to protect vulnerable patient groups from infection.

Other examples of microbial infections include, but are not limited to, bacterial pneumonias such as ventilator-associated pneumonia, and cystic fibrosis-associated infections.

Examples of fungal infections include, but are not limited to, invasive pulmonary aspergillosis and invasive pulmonary candidiasis, *Pneumocystis carinii* pneumonia, and *Coccidioides* and *Crytococcus* infections, e.g., in immunosuppressed patients.

Examples of viral conditions treatable according to the present invention include, but are not limited to, pulmonary viral infections such as respiratory syncytial virus bronchiolitis, especially in infants and the elderly, or influenza virus, or rhino virus. Numerous studies have shown that during the progression of AIDS, mononuclear cells lose their ability to secrete IL-2, IL-12 and IFN-γ and produce increased levels of IL-4, which allows the HIV virus to proliferate. Therefore treatment with CMP, given intranasally or by inhalation, will be useful in reducing the progression of HIV infection by restoring IL-12 and IFN-γ levels.

In one embodiment, the condition treatable according to the present invention may be cancer, especially where the cancer is caused by an infectious agent and can be treated because the present invention is capable of upregulating the immune system to attack the cancer or the infectious agent (e.g., a virus) that causes it. It is now known that infectious agents can cause cancer; for example human papillomavirus (HPV) has been shown to cause cervical cancer in women, and vaccination against HPV has been shown to be an effective way of treating or helping to prevent cervical cancer. HPV is responsible for 70% of cervical cancers, and the vaccine Gardasil has been approved for the prophylactic treatment of cervical cancer. Gardasil contains recombinant virus like particles assembled from the L1 proteins of HPVs 6, 11, 16 and 18. In a further embodiment, the present invention may include compositions and their medical uses in which the antigen from an infectious agent is provided by a Gardasil composition, in combination with the further adjuvant and the CMP preparation. By way of further example, vaccines against hepatitis B virus (HBV) have been shown to ameliorate an individual's risk of getting liver cancer. The use of such vaccines in combination with a CMP preparation and a further adjuvant is an aspect of the present invention.

Other approaches to making cancer vaccines that may be employed in conjunction with the present invention include the use of antigens which are cancer cells, parts of cancer cells, or cancer cell antigens. The vaccine may increase the immune response against cancer cells that are already present in the body and generally have the advantage that they are specific for the particular form of cancer from which the antigen is derived.

The invention will now be further described by way of the following non-limiting examples which further illustrate the invention, and are not intended, nor should they be interpreted to, limit the scope of the invention.

EXAMPLES

Example 1

Materials and Methods

Mice

BALB/c mice (6-8 week old, n=4/group) were used.

Immunizations

Immunizations were given intranasally in a total of 20 microlitres containing 10 micrograms of merozoite surface protein 1 (MSP1$_{19}$) mixed with 100 micrograms chitin microparticles (CMP) and 5 micrograms cholera toxin B subunit (CTB) where indicated.

Immunization Protocols

For antibody measurements, mice were immunized on days 0, 21, 42 and 56. Specific immunoglobulin G (IgG) was measured 28 days after the last immunization.

Comparisons were made between different immunization protocols for the combined vaccine (MSP1, CTB, CMP) when given twice over 3 weeks, twice a week for 3 weeks, or three times a week for 3 weeks. For challenge studies, mice were immunized intranasally on days 0, 14, 28, and 42.

P. yoelii Challenge

Challenge was by i.v. injection of 1×10$^4$ live P. yoelii YM parasitized red blood cells (pRBC) given 30 days after the last immunization. Parasitaemia was monitored daily by microscopic analysis of the % infected red blood cells taken from tail blood samples. A minimum of 10,000 cells were counted. The survival of the mice was observed.

Results

Survival from P. yoelii Challenge

The survival from nasal vaccination with the soluble MSP1 antigen did not enhance survival and all four mice were dead by day 10 post infection. Vaccination with MSP1 and either CTB or CMP as adjuvant did not improve this outcome significantly. However, vaccination with the peptide mixed with both CMP and CTB did lead to significant enhancement in protection with 3 of the 4 mice surviving past day 15 post infection (Table 1). These mice continued to live until day 30 after which they were killed.

Anti-MSP1$_{19}$ Antibody Titre

Figure 1:
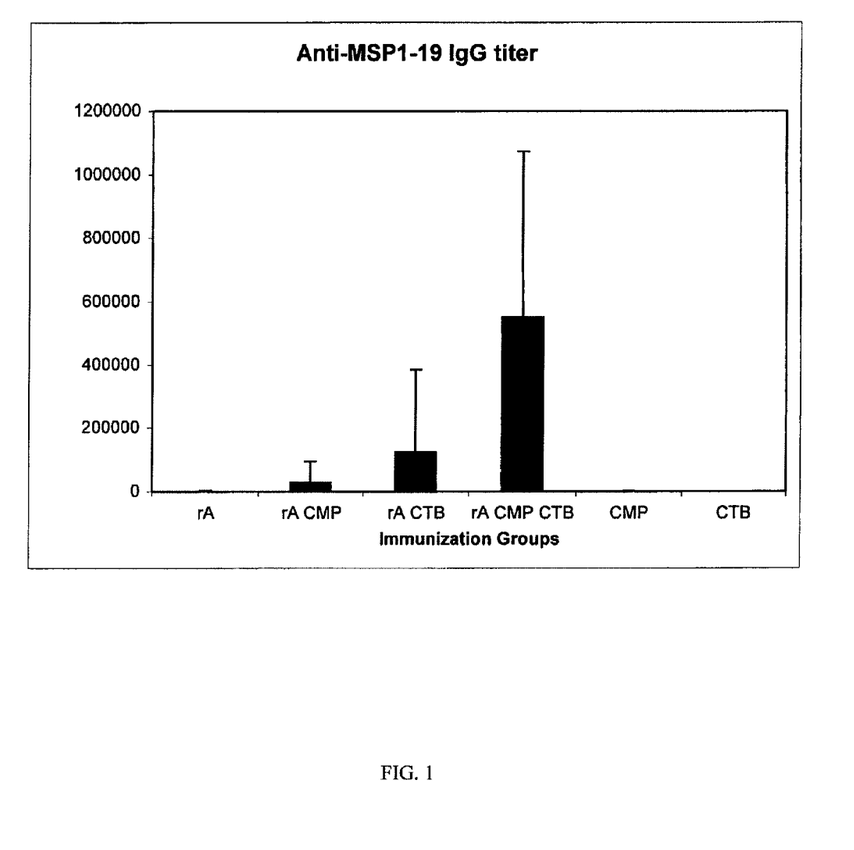
FIG. 1 shows the anti-merozoite surface protein 1 ($MSP1_{19}$) immunoglobulin G (IgG) titer in mice immunized on days 0, 21, 42 and 56. $MSP1_{19}$ IgG was measured 28 days after the last immunization. rA=$MSP1_{19}$. (n=4 per group)

Mice were immunized on days 0, 21, 42, and 56. The anti-MSP1$_{19}$ antibody titre was determined 28 days after the last immunization. Intranasal vaccination with recombinant antigen (rA) MSP1$_{19}$ alone did not induce significant specific IgG production. The addition of CTB adjuvant produced a better response, but although the highest antibody titre was achieved by the combined vaccine with both CTB and CMP adjuvants, which generated 4 times more IgG than CTB alone (FIG. 1.). Either adjuvant administered alone did not lead in specific IgG.

Immunization Protocols

To test the effect of the frequency of immunization with the combined vaccine (10 μg MSP1$_{19}$+5 μg CTB+100 μg CMP), three different protocols were tested:

(1) Twice in 3 weeks ("IN2-2"), a total of 2 intranasal immunizations.

(2) Twice per week for 3 weeks ("IN2-6"), a total of 6 intranasal immunizations.

(3) Three times per week for 3 weeks ("IN3-9"), a total of 9 intranasal immunizations.

IgG titres were measured 28 days after the last immunization.

Figure 2:
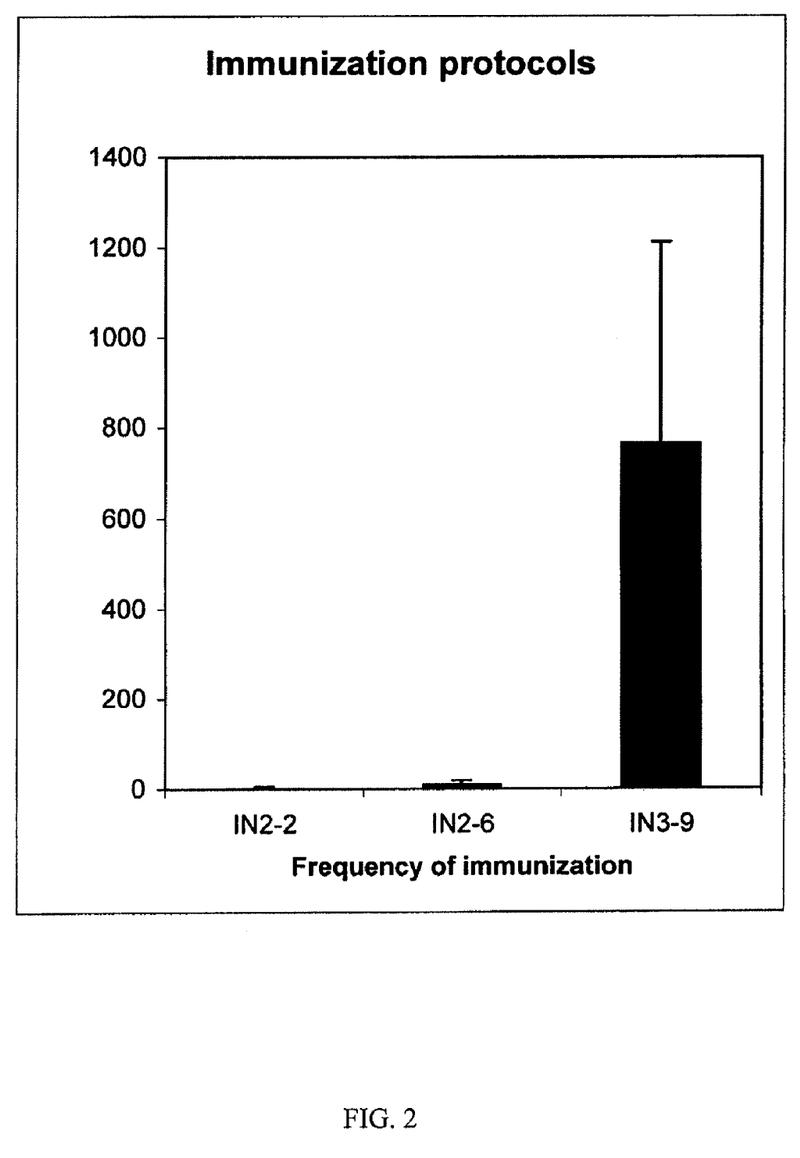
FIG. 2 shows the effect of the frequency of immunization: twice in 3 weeks (IN2-2), a total of 2 intranasal immunizations; twice per week for 3 weeks (IN2-6), a total of 6 intranasal immunizations; three times per week for 3 weeks (IN3-9), a total of 9 intranasal immunizations. (n=4 per group)

The effect of the frequency of immunization are shown in FIG. 2. The protocol with a more frequent vaccination of 3 times per week for 3 week was the only protocol to produce a significant IgG titre (P<0.05).

Discussion

The experimental data indicates a potential malaria vaccine which can be delivered intranasally. The findings show that the nasal adjuvants CTB and CMP interact synergistically. The addition of chitin microparticles (CMP) improves the efficacy of the nasal vaccine. This is an important finding because production of an effective subunit vaccine requires the addition of a potent adjuvant to stimulate an immune response and to overcome the natural immune tolerance threshold to antigens, particularly to simple recombinant peptide fragments, which lack the complex 3D structure of a mature protein. Many such subunit vaccines are limited because of the toxicity and local reactions associated with the addition of such a potent adjuvant or of the addition of large amounts of adjuvant needed to elicit the desired immune response. CMP is a relatively innocuous material and non-inflammatory, and unlikely to cause such local or systemic reactions. The finding that the addition of CMP improves the efficacy of a vaccine is an important contribution to vaccine design.

The experimental data further shows that nasal vaccination is highly influenced by the frequency with which the vaccine is administered. This is probably due to the natural unresponsiveness of the nasal mucosa to foreign proteins, an adaptation necessary to prevent unneeded immune responses to innocuous airborne particles that constantly bombard the mucosa. These findings indicate specifically that a protocol of immunization of 3 times/week for 3 weeks is particularly effective.

TABLE 1

The survival rate of mice immunized intranasally with different MSP1$_{19}$ vaccine formulates. CMP = chitin microparticles; CTB = cholera toxin B subunit; MSP1$_{19}$ = 19 kilodalton-carboxyl terminal fragment of merozoite surface protein-1. Groups of four BALB/c mice were immunized intranasally with MSP1$_{19}$ plus CMP or CTB or both CMP and CTB on day 0, 14, 28, and 42. Mice were challenged with 1 × 10$^4$ P. yoelii-pRBC per mouse 30 days following the last immunization.

| Vaccine formulation | Survival (survived/total) | Date of death |
|---|---|---|
| MSP1$_{19}$ | 0/4 | 10, 9, 9, 10 |
| MSP1$_{19}$ + CMP | 0/4 | 9, 10, 11, 11 |
| MSP1$_{19}$ + CTB | 1/4 | 11, 11, 12 |
| MSP1$_{19}$ + CMP + CTB | 3/4 | 15 |

TABLE 1-continued

The survival rate of mice immunized intranasally with different MSP1$_{19}$ vaccine formulates. CMP = chitin microparticles; CTB = cholera toxin B subunit; MSP1$_{19}$ = 19 kilodalton-carboxyl terminal fragment of merozoite surface protein-1. Groups of four BALB/c mice were immunized intranasally with MSP1$_{19}$ plus CMP or CTB or both CMP and CTB on day 0, 14, 28, and 42. Mice were challenged with $1 \times 10^4$ P. yoelii-pRBC per mouse 30 days following the last immunization.

| Vaccine formulation | Survival (survived/total) | Date of death |
|---|---|---|
| CMP | 0/4 | 15, 16, 15, 4 |
| CTB | 1/4 | 14, 14, 9 |

The invention is further described by the following numbered paragraphs:

Paragraph 1: A composition comprising an antigen from an infectious agent, a chitin microparticle preparation (CMP) and a further adjuvant.

Paragraph 2: The composition according to paragraph 1, wherein the composition is a vaccine composition.

Paragraph 3: The composition according to paragraph 1 or paragraph 2, wherein the infectious agent mediates a bacterial infection, a fungal infection, a viral infection or a parasitic infection.

Paragraph 4: Use of a composition comprising an antigen from an infectious agent, a chitin microparticle preparation (CMP) and a further adjuvant for the preparation of a medicament for the prophylaxis or treatment of a condition mediated by the infectious agent.

Paragraph 5: The use according to paragraph 4, wherein the condition is a bacterial infection, a fungal infection, a viral infection or a parasitic infection.

Paragraph 6: The use according to paragraph 4 or paragraph 5, wherein the medicament is for administration to a patient at least two times per week.

Paragraph 7: The use according to paragraph 6, wherein the medicament for administration to the patient at least three times per week.

Paragraph 8: The use according to any one of paragraphs 4 to 7, wherein the medicament is for administration via a mucosal or a non-mucosal delivery route.

Paragraph 9: The use according to paragraph 8, wherein the mucosal delivery route is intranasal delivery, sublingual delivery, oral delivery, delivery in eye drops or delivery by inhalation.

Paragraph 10: The use according to paragraph 8, wherein the non-mucosal delivery route is delivery by injection.

Paragraph 11: The use according to paragraph 10, wherein the injection is subcutaneous injection or intramuscular injection.

Paragraph 12: The use according to any one of paragraphs 4 to 11, wherein the medicament is for prophylactic administration to a patient at risk of infection.

Paragraph 13: The use according to paragraph 12, wherein the patient at risk is an elderly person, a premature baby, an infant, a transplantation patient, an immunosuppressed patient, a chemotherapy patient, a hospital patient at risk of opportunistic infection, a patient on a ventilator, a cystic fibrosis patient or a patient with AIDS.

Paragraph 14: The use according to any one of paragraphs 6 to 13, wherein the condition is a bacterial infection by Pseudomonas aeruginosa, a Streptococcus species, Haemophilus influenza, Klebsiella pneumoniae, Yersinia enteocolitica, Salmonella, Listeria, a Mycobacteria species.

Paragraph 15: The use according to paragraph 14, wherein the Streptococcus species is Streptococcus pneumoniae, Streptococcus pyrogenes or Streptococcus agalactiae.

Paragraph 16: The use according to paragraph 14, wherein the Mycobacterial species is Mycobacterium tuberculosis or Mycobacterium leprae.

Paragraph 17: The use according to any one of paragraphs 5 to 15, wherein the condition is bacterial pneumonia such as ventilator-associated pneumonia or cystic fibrosis associated infections.

Paragraph 18: The use according to any one of paragraphs 5 to 15, wherein the condition is Otitis media.

Paragraph 19: The use according to any one of paragraphs 5 to 13, wherein the parasitic infection is an infection by a Leishmania species and Schistosoma species or a Plasmodium species.

Paragraph 20: The use according to any one of paragraphs 5 to 13, wherein the fungal infection is invasive pulmonary aspergillosis and invasive pulmonary candidiasis, Pneumocystis carinii pneumonia, or a Coccidioides or Crytococcus.

Paragraph 21: The use according to any one of paragraphs 5 to 13, wherein the condition is a pulmonary viral infection.

Paragraph 22: The use according to paragraph 21, wherein the viral infection is caused by infection by respiratory syncytial virus bronchiolitis, influenza virus, rhino virus or human immunodeficiency virus (HIV).

Paragraph 23: The use according to any one of paragraphs 5 to 12, wherein the condition is cancer.

Paragraph 24: The use according to paragraph 23, wherein the cancer is caused by a virus.

Paragraph 25: The use according to paragraph 24, wherein the virus is human papillomavirus and the condition is cervical cancer or the virus is hepatitis B virus and the condition is liver cancer.

Paragraph 26: The use according to any one of paragraphs 3 to 25, wherein the chitin microparticles have an average diameter of less than 110 μm.

Paragraph 27: The use according to paragraph 26, wherein the chitin microparticles have an average diameter of less 5 μm.

Paragraph 28: The use according to paragraph 27, wherein the chitin microparticles have an average size of at least 1 μm in diameter.

Paragraph 29: The use according to any one of paragraphs 3 to 28, wherein the chitin microparticles are derived from the exoskeletons of crab, shrimp, lobster, cuttlefish, and insects and fungi.

Paragraph 30: The use according to any one of paragraphs 3 to 29, wherein the chitin microparticles are obtainable by sonicating or milling purified chitin.

Paragraph 31: The use according to any one of paragraphs 3 to 30, wherein the chitin microparticles are obtainable by coating carrier particles with N-Acetyl-D-Glucosamine, chitin or a fragment thereof.

Paragraph 32: The use according to any one of paragraphs 3 to 31, wherein the units forming the chitin in the CMP composition which are deacetylated comprise less than 20% of the total units.

Paragraph 33: The use according to any one of paragraphs 3 to 32, the medicament for administration to a patient in an amount of between 0.01 and 100 mg of active compound per kg of body weight.

Paragraph 34: The use according to any one of paragraphs 3 to 33, wherein the medicament is for human administration.

Paragraph 35: The use according to any one of paragraph 3 to 34, wherein the chitin microparticle preparation comprises one or more of a pharmaceutically acceptable excipient, a carrier, a propellant, a buffer, a stabiliser, an isotonicizing agent, a preservative or an antioxidant.

Paragraph 36: A delivery device for the administration of the chitin microparticles comprising:
a) a reservoir of a composition according to any one of paragraphs 1 to 3;
b) a delivery orifice adapted to locate in a patient's mouth or nose; and
c) a valve between the reservoir and the delivery orifice such that the valve can be operated to control delivery of the chitin microparticles.

Paragraph 37: A kit comprising:
a) a chitin microparticle preparation;
b) an antigen from an infectious agent; and
c) a further adjuvant;
for simultaneous or sequential administration to a patient for providing immunity against the condition that the organism causes.

Paragraph 38: A kit according to paragraph 37, further comprising a delivery device.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

REFERENCES

The references mentioned herein are all expressly incorporated by reference. Citation or identification of any document in this application is not an admission that such document is available as prior art to the present invention.
1. Shibata et al, J. Immunol., 164: 1314-1321, 2000.
2. Shibata et al, J. Immunol., 161: 4283-8, 1998.
3. Shibata et al, Infection and Immunity, 65(5): 1734-1741, 1997.
4. Shibata et al, J. Immunol., 159: 2462-2467, 1997.
5. Horan et al, Mor. Mortal. Wkly. Rep. CDC Surveill. Summ., 35: 17SS-29SS, 1986.
6. Davies J., Nature, 383: 219-220, 1996.
7. Katare et al, Vaccine, 24:3599-608, 2006
8. Siddiqui et al, Proc. Natl. Acad. Sci., 84:3014, 1987
9. Hirunpetcharat et al, Parasite Immunol., 20:413-420, 1998
10. Fujioka et al, Malaria: Molecular and Clinical aspects, 199
Japanese Patent Application No: 19997-0087986 A (Unitika Limited).
U.S. Pat. No. 5,591,441 9 (Medical Sciences Research Institute).
WO 03/015744 (Medical Research Council).
WO 98/30207 (Danbiosyst Limited).
WO 97/20576 (Danbiosyst Limited).
WO 90/09780 (Danbiosyst Limited).

What is claimed is:
1. A composition comprising an antigen from an infectious agent, a chitin microparticle preparation (CMP) and a further adjuvant, wherein the further adjuvant does not comprise chitin.
2. The composition according to claim 1, wherein the composition is an immunogenic composition.

3. The composition according to claim 1, wherein the infectious agent mediates a bacterial infection, a fungal infection, a viral infection or a parasitic infection.
4. A method of treating a condition mediated by an infectious agent in a patient comprising administering a composition comprising an antigen from an infectious agent, a chitin microparticle preparation (CMP) and a further adjuvant, wherein the further adjuvant does not comprise chitin.
5. The method according to claim 4, wherein the condition is a bacterial infection, a fungal infection, a viral infection or a parasitic infection.
6. The method according to claim 4, wherein the composition is administered to a patient at least two times per week.
7. The method according to claim 6, wherein the composition is administered to the patient at least three times per week.
8. The method according to claim 4, wherein the composition is administered via a mucosal or a non-mucosal delivery route.
9. The method according to claim 8, wherein the mucosal delivery route is intranasal delivery, sublingual delivery, oral delivery, delivery in eye drops or delivery by inhalation.
10. The method according to claim 8, wherein the non-mucosal delivery route is delivery by injection.
11. The method according to claim 10, wherein the injection is subcutaneous injection or intramuscular injection.
12. The method according to claim 4, wherein the composition is administered to a patient at risk of infection.
13. The method according to claim 12, wherein the patient at risk is an elderly person, a premature baby, an infant, a transplantation patient, an immunosuppressed patient, a chemotherapy patient, a hospital patient at risk of opportunistic infection, a patient on a ventilator, a cystic fibrosis patient or a patient with AIDS.
14. The method according to claim 4, wherein the condition is a bacterial infection-by *Pseudomonas aeruginosa*, a *Streptococcus* species, *Haemophilus influenza*, *Klebsiella pneumoniae*, *Yersinia enteocolitica*, *Salmonella*, *Listeria*, a *Mycobacteria* species.
15. The method according to claim 14, wherein the *Streptococcus* species is *Streptococcus pneumoniae*, *Streptococcus pyrogenes* or *Streptococcus agalactiae*.
16. The method according to claim 14, wherein the Mycobacterial species is *Mycobacterium tuberculosis* or *Mycobacterium leprae*.
17. The method according to claim 4, wherein the condition is bacterial pneumonia or cystic fibrosis associated infections.
18. The method according to claim 4, wherein the condition is Otitis media.
19. The method according to claim 4, wherein the condition is a parasitic infection.
20. The method according to claim 4, wherein the condition is a fungal infection.
21. The method according to claim 4, wherein the condition is a pulmonary viral infection.
22. The method according to claim 21, wherein the viral infection is caused by infection by respiratory syncytial virus bronchiolitis, influenza virus, rhino virus or human immunodeficiency virus (HIV).
23. The method according to claim 19, wherein the parasitic infection is caused by a *Leishmania* species and *Schistosoma* species or a *Plasmodium* species.
24. The method according to claim 20, wherein the fungal infection is caused by invasive pulmonary aspergillosis and invasive pulmonary candidiasis, *Pneumocystis carinii* pneumonia, or a *Coccidioides* or *Crytococcus*.

25. The method according to claim 4, wherein the chitin microparticles have an average diameter of less than 10 μm.

26. The method according to claim 25, wherein the chitin microparticles have an average diameter of less 5 μm.

27. The method according to claim 26, wherein the chitin microparticles have an average size of at least 1 μm in diameter.

28. The method according to claim 4, wherein the chitin microparticles are derived from the exoskeletons of crab, shrimp, lobster, cuttlefish, and insects and fungi.

29. The method according to claim 4, wherein the chitin microparticles are obtainable by sonicating or milling purified chitin.

30. The method according to claim 4, wherein the chitin microparticles are obtainable by coating carrier particles with NAcetyl-D-Glucosamine, chitin or a fragment thereof.

31. The method according to claim 4, wherein the units forming the chitin in the CMP composition which are deacetylated comprise less than 20% of the total units.

32. The method according to claim 4, wherein the composition is administered in an amount of between 0.01 and 100 mg of active compound per kg of body weight.

33. The method according to claim 4, wherein the composition is administered to a human.

34. The method according to claim 4, wherein the chitin microparticle preparation comprises one or more of a pharmaceutically acceptable excipient, a carrier, a propellant, a buffer, a stabiliser, an isotonicizing agent, a preservative or an antioxidant.

35. A kit comprising:
a) a chitin microparticle preparation;
b) an antigen from an infectious agent; and
c) a further adjuvant, wherein the further adjuvant is an adjuvant which is different than the CMP preparation.

36. A kit according to claim 35, further comprising a delivery device.

37. The method according to claim 17, wherein the bacterial pneumonia is ventilator-associated pneumonia.

* * * * *